United States Patent [19]

della Valle

[11] 4,362,741
[45] Dec. 7, 1982

[54] THERAPEUTIC COMPOSITION FOR PREVENTING THE AGGREGATION OF PLATELETS

[75] Inventor: Francesco della Valle, Padua, Italy

[73] Assignee: FIDIA, S.p.A., Padua, Italy

[21] Appl. No.: 224,452

[22] Filed: Jan. 12, 1981

Related U.S. Application Data

[63] Continuation-in-part of Ser. No. 101,005, Dec. 6, 1979, abandoned.

[30] Foreign Application Priority Data

Dec. 19, 1978 [IT] Italy .............................. 30992 A/78

[51] Int. Cl.$^3$ .............................................. A61K 31/37
[52] U.S. Cl. ..................................................... 424/281
[58] Field of Search ......................................... 424/281

[56] References Cited

PUBLICATIONS

Chem. Abst. 86 72440(s) (1977), Giermasionski et al.
Chem. Abst. 86 155,515(w) (1977), Stankevics et al.

Primary Examiner—Douglas W. Robinson
Attorney, Agent, or Firm—Birch, Stewart, Kolasch and Birch

[57] ABSTRACT

A composition for preventing the aggregation of platelets comprising, as an essential ingredient thereof, 8-bromo- or 8-chloro-3-($\beta$-diethylaminoethyl)-4-methyl-7-ethoxycarbonylmethoxycoumarin, and the use thereof.

6 Claims, No Drawings

THERAPEUTIC COMPOSITION FOR PREVENTING THE AGGREGATION OF PLATELETS

BACKGROUND OF THE INVENTION

Cross-Reference to Related Application

This application is a continuation-in-part of copending application Ser. No. 101,005, filed on Dec. 6, 1979, now abandoned.

FIELD OF THE INVENTION

The present invention relates to a new therapeutic application of 8-chloro- or 8-bromo-3-($\beta$-diethylaminoethyl)-4-methyl-7-ethoxycarbonylmethoxycoumarin of the formula:

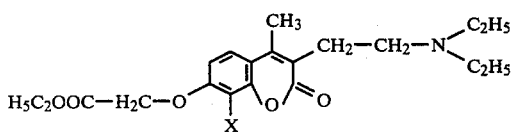

wherein X is a chlorine or bromine atom. These compounds, or pharmaceutically acceptable salts thereof, were obtained for the first time in the pure state by means of highly selective processes developed by the present applicant.

Said 8-chloro and 8-bromocoumarin derivatives possess vasodilating coronary activity which is superior to that of carbochromene, as well as antiarrhythmic properties. Such properties are made possible by the selective methods of preparation described and claimed by the present inventor in copending application Ser. No. 952,460, filed on Oct. 18, 1978 (now abandoned), which permits selective halogenation at a single and predetermined position on the coumarin molecule, thus yielding a product free of impurities. Specifically, these compounds contain a chloro or bromo moiety at the 8-position of the molecule.

There has now been discovered and ascertained another property of the 8-bromo or 8-chlorocarbochromene compounds. That is, in accordance with the present invention, it has been found that said compounds have a marked activity against the aggregation of platelets, both in vitro and in vivo.

The case of compounds having more than one pharmacological activity is well known and, as an example thereof, there may be cited dipyridamole which, in addition to having a vasodilating activity, also has the property of being active against platelet aggregation.

In order to better illustrate the anti-aggretative activity of said compounds, there is set forth below by way of example the description of some of the tests which have been carried out.

Evidence of platelet anti-aggregative activity in vitro and in vivo

The following are the experimental conditions and methods which were used for measuring platelet anti-aggregative activity.

(a) In vitro experiment

For the in vitro experiment, blood was drawn from rabbits of the pure New Zealand strain having a weight of 2.0–2.5 kg by intracardiac injection containing 1 ml of sodium citrate at 3.8% (9 ml); the mixture was then centrifuged for 10 minutes at 121 g (1,000 rpm), thereby obtaining about 3 ml of platelet rich plasma (PRP).

The remaining blood was centrifuged again at 12,100 g (10,000 rpm) for 10 minutes; platelets poor in plaques (PPP) was thus obtained.

There were then prepared with the PRP, suitably diluted with PPP, samples containing 300,000 platelets per $mm^3$, which were counted in a Burker chamber.

Increasing doses of the test compound were then added thereto, ranging from $5\gamma$/ml to $200\gamma$/ml in vitro. The comparison products used were ditazol and dipyridamole, at the same doses. The aggregating activity of the platelets was measured with a Born aggregometer, by the addition of $0.5\gamma$/ml of ADP (adenosine diphosphate) (1 mM).

The activity was calculated as the percent (%) inhibition of the aggregation.

The results are shown in the following Table.

TABLE 1

| Dosage $\gamma$/ml | Platelet anti-aggregative activity in vitro % inhibition | | |
|---|---|---|---|
| | Ditazol | Dipyridamole | 8-chloro-3-($\beta$-diethylaminoethyl)-4-methyl-7-ethoxycarbonylmethoxycoumarin hydrochloride |
| 5 | — | — | 20 |
| 10 | — | — | 60 |
| 25 | 10 | 8 | 70 |
| 50 | 50 | 35 | 84 |
| 100 | 100 | 90 | 100 |
| 200 | 100 | 100 | 100 |

(b.1) Anti-aggregative activity under normal conditions in vivo

Rabbits of the pure New Zealand strain having a weight of 2.0–2.5 kg, were used to evaluate the platelet anti-aggregative activity under normal conditions.

The animals, fed with a standard diet, were treated for two weeks with the test compound by the intravenous route; the activity of the substance was compared with that of a product having a known platelet anti-aggregative activity, acetylsalicylic acid (lysine salt).

The determinations were effected on the plasma of the rabbits obtained as explained hereinafter.

The blood (9 ml) was drawn by intracardiac injection in a syringe containing 1 ml of sodium citrate at 3.8%. The mixture was then centrifuged for 10 minutes at 121 g (1,000 rpm), thereby obtaining about 3 ml of plasma rich in plaques (PRP).

The remaining blood was then centrifuged again at 12,100 g (10,000 rpm) for 10 minutes; there was thus obtained the plasma poor in platelets (PPP).

There were then prepared with the PRP, suitably diluted with PPP, samples containing 300,000 platelets per $mm^3$, which were counted in a Burker chamber.

The aggregating activity of the platelets was measured with a Born aggregometer, with the addition of variable quantities of ADP, until a standard aggregation curve (Born G.V.P., Nature, 194, 927, 1962) is obtained.

The results are reported in the following Table.

TABLE 2

| Platelet anti-aggregative activity under normal conditions | | |
|---|---|---|
| Substance | Dosage mg/Kg i.v. | $\mu$l ADP 1 mM |
| Isotonic solution | 0.2 | 1.51 ± 0.48 |
| 8-chloro-3-($\beta$-diethylaminoethyl)-4-methyl-7-ethoxycarbonylmethoxy | 4 | 4.72 ± 0.55 |

TABLE 2-continued

| Platelet anti-aggregative activity under normal conditions | | |
|---|---|---|
| Substance | Dosage mg/Kg i.v. | μl ADP 1 mM |
| coumarin hydrochloride | | |
| Acetylsalicylic acid in the form of the lysine salt | 4 | 4.51 ± 0.30 |

(b.2) Anti-aggregative activity under pathological conditions following an atherogeneous diet in vivo The experiments were conducted in rabbits of the pure New Zealand strain having a weight of about 2.0–2.5 kg.

The animals were fed for eight weeks with an atherogeneous diet containing 1% of cholesterol, so as to obtain a dislipidermic picture and to determine a platelet hyperaggregability, as described in the literature (K. Oversohl et al., Thromb. Res. 7, 481, 1975).

At the same time, the animals were treated with the test product which was administered intravenously.

The anti-aggregative activity of the 8-halo derivative of the invention was compared with that of a pharmaceutical product having a known anti-aggregative activity, i.e., acetylsalicylic acid (as the lysine salt).

The determinations were made on the plasma of the rabbits, obtained as hereinafter described.

The blood (9 ml) was drawn by intracardiac injection in a syringe containing 1 ml of sodium citrate at 3.8%; the mixture was then centrifuged for 10 minutes at 121 g (1,000 rpm), thereby obtaining about 3 ml of a platelet rich plasma (PRP).

The remaining blood was then centrifuged again at 12,100 g (10,000 rpm) for 10 minutes, thus providing platelet poor plasma (PPP).

Samples containing 300,000 platelets per $mm^3$, which were counted in a Burker chamber, were then prepared with the PRP, suitably diluted with PPP.

The aggregative activity of the platelets was measured with a Born aggregometer, with the addition of variable quantities of ADP, until a standard aggregation curve was obtained (Born G.V.P., Nature, 194, 927, 1962).

The results are set forth in Table 3.

TABLE 3

| Platelet anti-aggregative activity in animals on an atherogeneous diet | | |
|---|---|---|
| Substance | Dosage mg/kg i.v. | μl ADP 1 mM |
| Isotonic solution | 0.2 | 0.38 ± 0.26 |
| 8-chloro-3-(β-diethylaminoethyl)-4-methyl-7-ethoxycarbonylmethoxy coumarin hydrochloride | 4 | 1.23 ± 0.51 |
| Acetylsalicylic acid, as the lysine salt | 4 | 1.19 ± 0.46 |

These results clearly show that the 8-chlorocoumarin derivative has a platelet anti-aggregative activity that is equal to or greater than that of acetylsalicylic acid which is, however, free of the undesirable collateral effects of this latter compound. Similar beneficial results can be obtained with the 8-bromocoumarin derivative.

The 8-chloro- or 8-bromocoumarin derivative employed in the present invention as a platelet anti-aggregative agent in mammals, as well as the pharmaceutically acceptable salts thereof such as the hydrochloride salt, can be utilized therapeutically orally or by injection. These compounds can be administered orally in different types of known preparations such as in the form of dragees, tablets or gelatin capsules as well as in other known forms and can be formulated in a manner well known to pharmaceutical chemists utilizing standard pharmaceutical excipients, carriers or diluents such as water, vegetable oils, syrup, gum arabic, gelatin, methylcellulose, polyglycols and others which may optionally be mixed with emulsifying agents. The compounds utilized in the present invention and the pharmaceutically acceptable salts thereof such as the hydrochloride salt may be injected intramuscularly or intravenously in the form of an injectable solution. The pharmaceutical preparations can be liquid or dried, for example lyophilized preparations, using suitable excipients or diluents which are well known to pharmaceutical chemists. Useful oral dosages for humans or animals are in the range of about 50–400 mg of active ingredient daily. Useful injection doses for said mammals are in the range of about 20–100 mg daily for intramuscular or intravenous injection.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for preventing the aggregation of platelets in mammals which comprise administering thereto an effective platelets anti-aggregative amount of a compound having the formula:

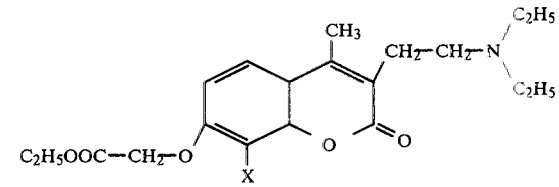

wherein X is chlorine or bromine, or a pharmaceutically acceptable salt thereof.

2. The method according to claim 1, wherein said compound is administered to a human or animal in an amount of about 50 to 400 mg. daily.

3. The method according to claim 1, wherein said compound is administered intramuscularly, or intravenously to a human or animal in an amount of about 20 to 100 mg. daily.

4. The method according to claim 1, wherein said salt is the hydrochloride salt.

5. The method according to claim 1, wherein said compound is 8-chloro-3-(β-diethylaminoethyl)-4-methyl-7-ethoxycarbonylmethoxycoumarin.

6. The method according to claim 1, wherein said compound is 8-bromo-3-(β-diethylaminoethyl)-4-methyl-7-ethoxycarbonylmethoxycoumarin.

* * * * *